(12) United States Patent
Wendelbo et al.

(10) Patent No.: US 7,533,587 B2
(45) Date of Patent: May 19, 2009

(54) METHOD AND APPARATUS FOR MASS ANALYSIS OF SAMPLES

(75) Inventors: Rune Wendelbo, Oslo (NO); Duncan E. Akporiaye, Oslo (NO); Arne Karlsson, Oslo (NO); Ib-Rune Johansen, Oslo (NO); Ivar M. Dahl, Oslo (NO); Britta G. Fismen, Oslo (NO); Richard Blom, Oslo (NO); Dag T. Wang, Oslo (NO); Morten Gulliksen, Oslo (NO); Martin Plassen, Oslo (NO)

(73) Assignee: UOP LLC, Des Plaines, IL (US)

( * ) Notice: Subject to any disclaimer, the term of this patent is extended or adjusted under 35 U.S.C. 154(b) by 168 days.

(21) Appl. No.: 11/767,603

(22) Filed: Jun. 25, 2007

(65) Prior Publication Data

US 2007/0245840 A1    Oct. 25, 2007

Related U.S. Application Data

(62) Division of application No. 10/833,594, filed on Jul. 1, 2004, now Pat. No. 7,279,131.

(51) Int. Cl.
*G01N 15/06* (2006.01)
*G01G 21/22* (2006.01)
*G01G 21/23* (2006.01)

(52) U.S. Cl. .......................... 73/865; 422/104; 422/50; 422/102; 422/99; 422/68.1; 73/772; 73/760; 436/174; 436/164; 436/166

(58) Field of Classification Search ........... 422/99–100, 422/102, 50, 104, 68.1; 436/173–174, 180, 436/164, 166, 148; 73/865, 760, 772
See application file for complete search history.

(56) References Cited

U.S. PATENT DOCUMENTS

| | | |
|---|---|---|
| 4,056,488 A | 11/1977 | Mitchell et al. |
| 4,566,326 A | 1/1986 | Lowell .................... 73/432 PS |
| 5,770,848 A * | 6/1998 | Oizumi et al. ......... 235/462.14 |
| 5,983,711 A | 11/1999 | Pappas et al. .................. 73/76 |
| 6,105,867 A * | 8/2000 | Shimizu et al. ............. 235/383 |
| 6,290,911 B1 | 9/2001 | Lewis et al. .............. 422/82.02 |
| 6,294,342 B1 | 9/2001 | Rohr et al. .................... 435/7.1 |
| 6,328,897 B1 * | 12/2001 | Leung ........................ 210/744 |
| 6,360,585 B1 | 3/2002 | Potyrailo et al. ........... 73/24.06 |
| 6,423,307 B2 | 7/2002 | Saettone et al. .......... 424/78.18 |
| 6,872,522 B1 | 3/2005 | Mecklenburg et al. ......... 435/6 |
| 6,886,746 B1 * | 5/2005 | Edwards ..................... 235/383 |
| 6,905,655 B2 | 6/2005 | Gabriel et al. ........... 422/82.01 |
| 7,025,714 B2 * | 4/2006 | Escal ............................. 494/1 |
| 7,325,667 B1 * | 2/2008 | Damick et al. .............. 198/395 |
| 2002/0028456 A1 | 3/2002 | Mansky et al. ................. 435/6 |
| 2002/0081587 A1 | 6/2002 | Hwang et al. .................. 435/6 |
| 2002/0094531 A1 | 7/2002 | Zenhausern ..................... 435/6 |
| 2002/0141901 A1 | 10/2002 | Lewis et al. .............. 422/82.01 |
| 2003/0186461 A1 | 10/2003 | Boehr et al. ................. 436/181 |
| 2003/0215816 A1 | 11/2003 | Sundararajan et al. ......... 435/6 |
| 2004/0071864 A1 | 4/2004 | Yao et al. ..................... 427/100 |
| 2004/0079651 A1 | 4/2004 | Kober et al. ............. 205/777.5 |
| 2004/0146434 A1 | 7/2004 | Kane et al. .................. 422/100 |

(Continued)

FOREIGN PATENT DOCUMENTS

| | | |
|---|---|---|
| WO | WO 00/20850 | 4/2000 |
| WO | WO 03/071241 | 8/2003 |

*Primary Examiner*—Brian R. Gordon
(74) *Attorney, Agent, or Firm*—Maryann Maas

(57) ABSTRACT

The present invention comprises an apparatus and a method for mass analyses of an array of samples contained in distinct sample holders. The sample holders are placed on a plurality of sensors which preferably comprise an array of microbalances providing output signals comprising mass data on the array of samples.

13 Claims, 4 Drawing Sheets

U.S. PATENT DOCUMENTS

| | | |
|---|---|---|
| 2004/0161861 A1 | 8/2004 | Levon et al. ............... 436/518 |
| 2005/0016276 A1 | 1/2005 | Guan et al. .................. 73/579 |
| 2005/0064581 A1 | 3/2005 | Manalis et al. ........... 435/287.2 |
| 2005/0118617 A1 | 6/2005 | Carlson ........................ 435/6 |
| 2005/0141587 A1 | 6/2005 | Muhlig et al. ................ 374/31 |
| 2005/0163191 A1 | 7/2005 | Carter et al. ............... 374/176 |
| 2005/0239847 A1 | 10/2005 | Bonifacio et al. ........ 514/355.5 |
| 2005/0261626 A1 | 11/2005 | Arai et al. ................ 604/96.01 |
| 2006/0014270 A1 | 1/2006 | Mansson et al. ......... 435/287.2 |
| 2006/0259163 A1 | 11/2006 | Hsiung et al. ................. 700/30 |
| 2006/0261161 A1* | 11/2006 | Murofushi et al. .......... 235/383 |
| 2009/0017764 A1* | 1/2009 | Bonner et al. .............. 455/66.1 |

* cited by examiner

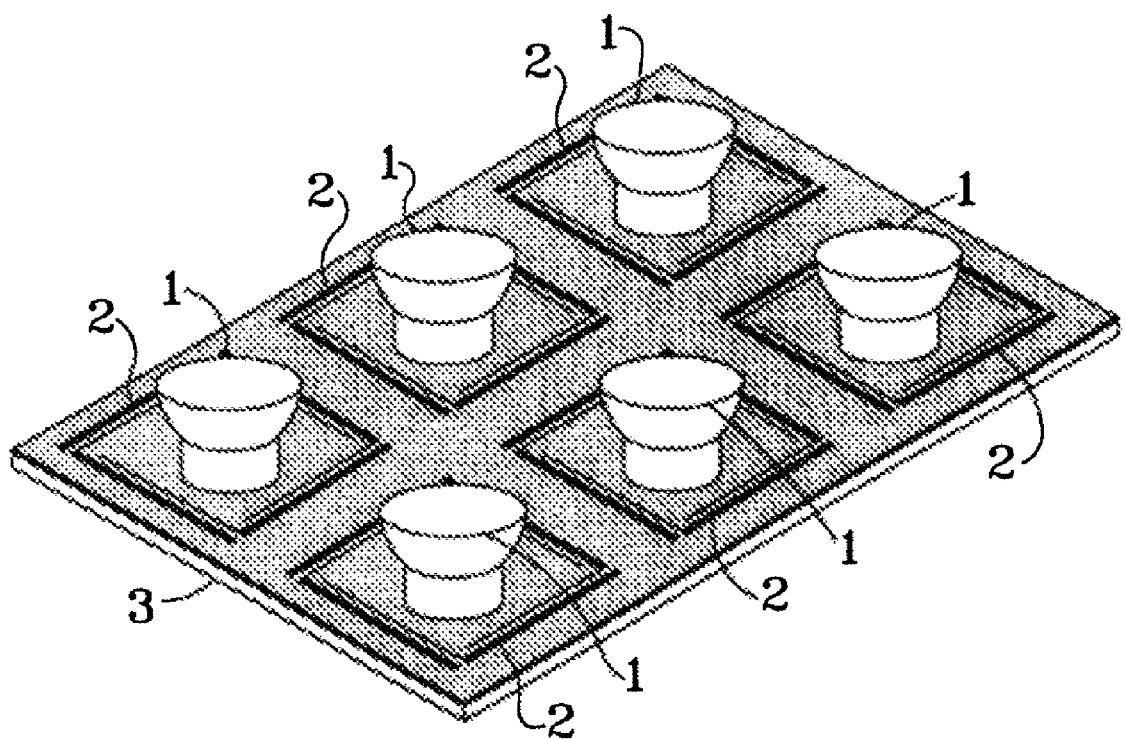
Fig. I

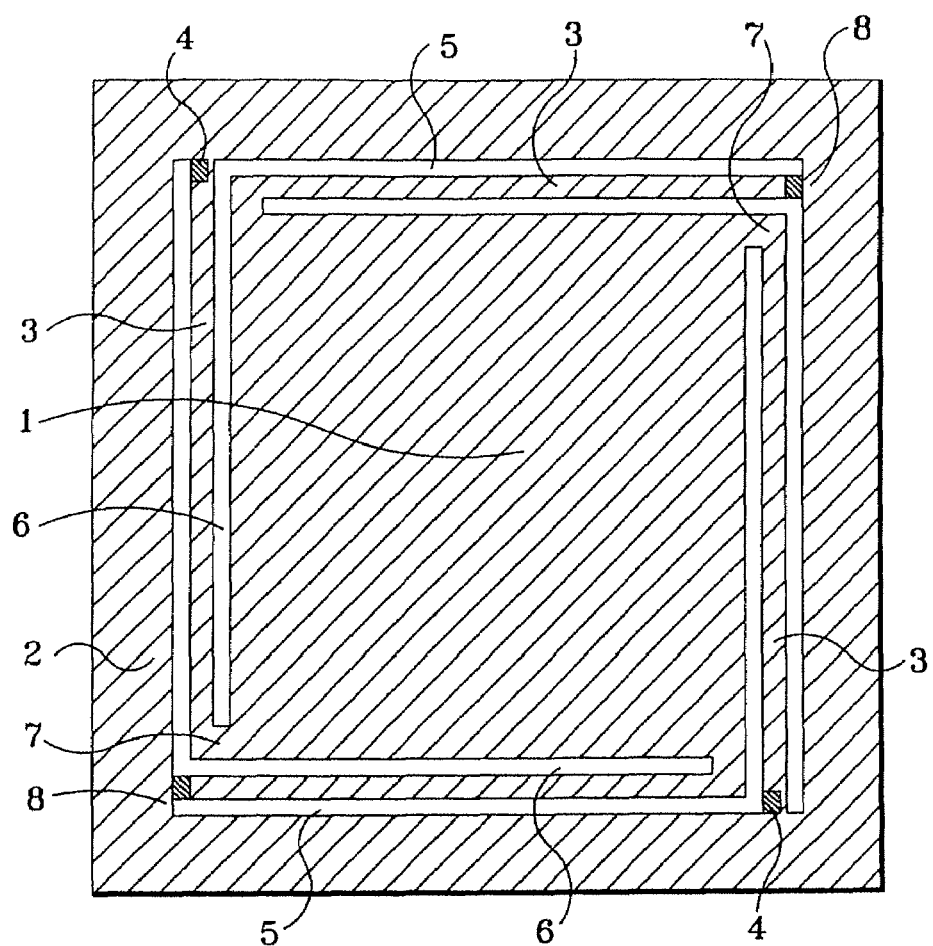
Fig. II
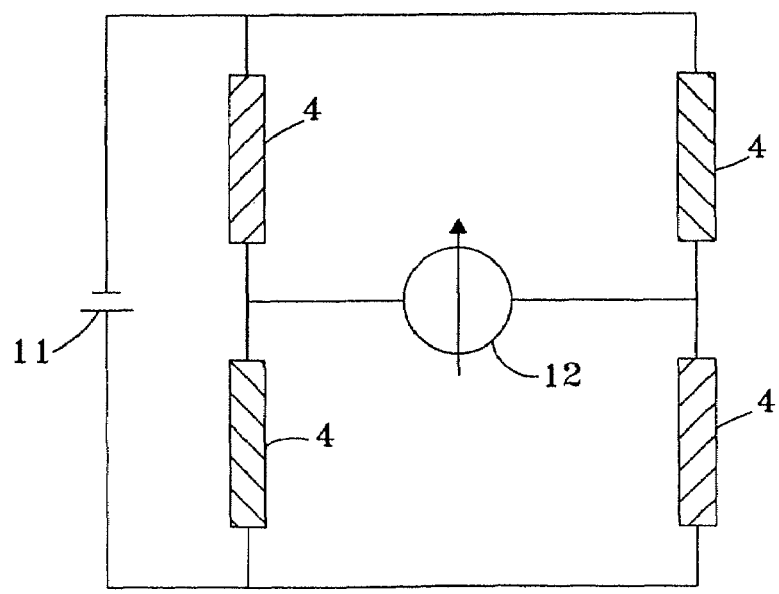
Fig. III

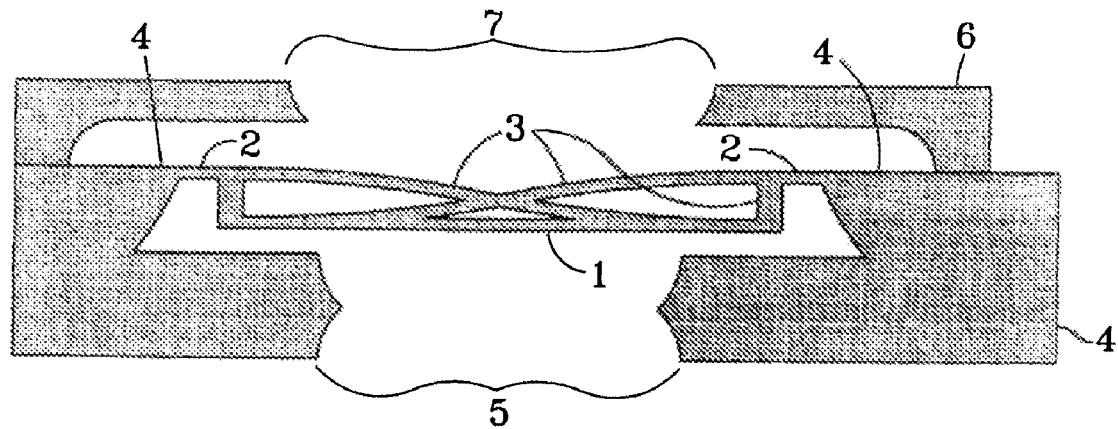
Fig. IV
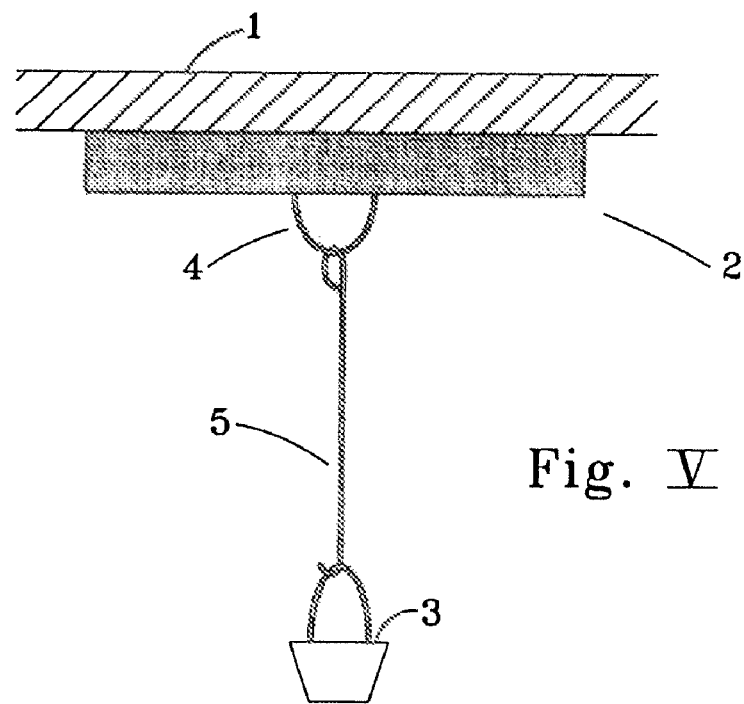
Fig. V

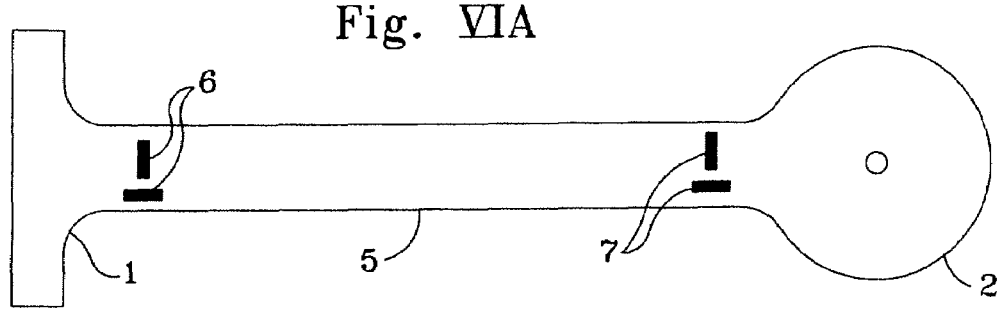
Fig. VIA
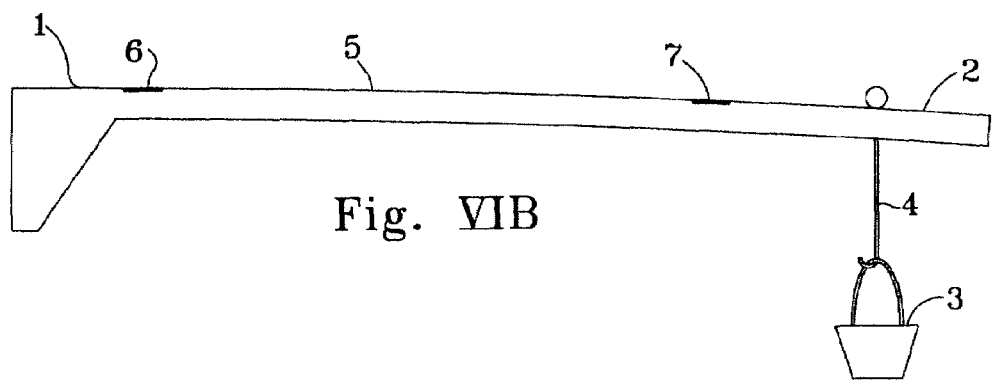
Fig. VIB
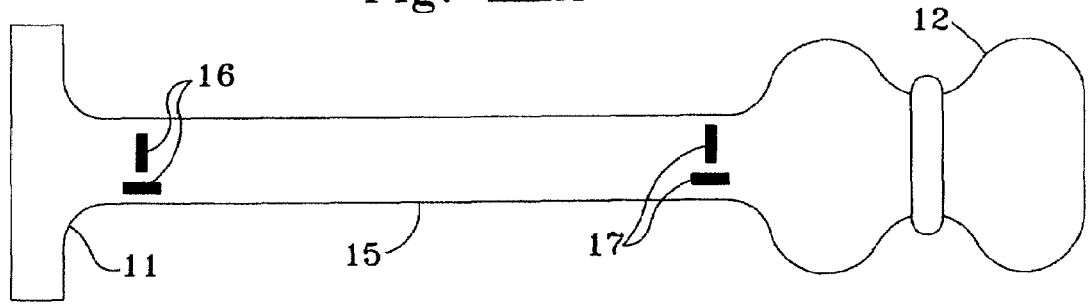
Fig. VIIA
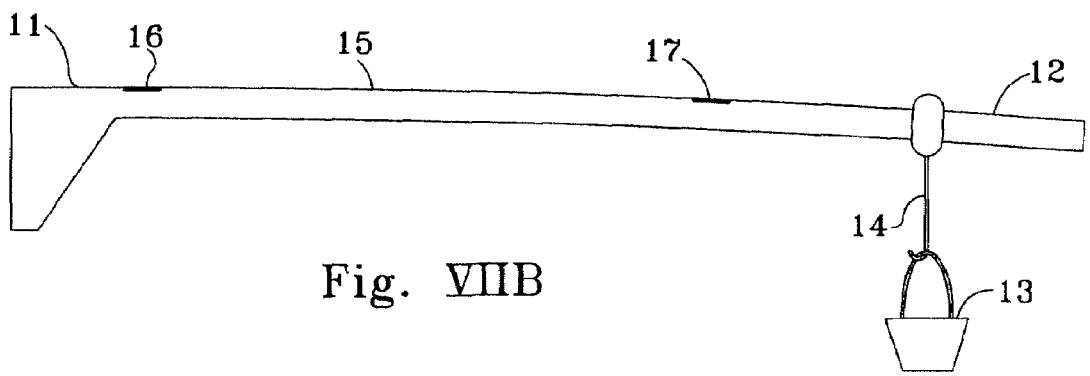
Fig. VIIB

METHOD AND APPARATUS FOR MASS ANALYSIS OF SAMPLES

CROSS-REFERENCE TO RELATED APPLICATION

This application is a Division of copending application Ser. No. 10/883,594 filed Jul. 1, 2004, the contents of which are hereby incorporated by reference in its entirety.

FIELD OF THE INVENTION

The present invention relates to the simultaneous measurement of mass properties of an array of samples. More specifically, the invention relates to the determination of the mass in the µg to gram range, but also in ranges higher or lower, of an array of samples.

BACKGROUND OF THE INVENTION

Gravimetric measurements at the laboratory scale have been hampered by relatively ponderous equipment and inefficient measurement speeds. There is a need for more efficient methods of monitoring and recording the mass of a number of materials in order to evaluate the properties of and/or screen and select optimum candidates for further development.

The optimization of materials for use in such applications as catalysts and adsorbents requires characterization of a large number of samples of such materials often as rapidly as possible. Analytical techniques for such characterization must be fast as well as accurate to deal with the large amount of data associated with the optimization. Parallel rather than serial measurement would facilitate rapid generation of data for such characterization. These measurements are particularly useful in the determination of properties or performance of, for example, surface properties such as surface area and pore diameter, which are indicators of potential performance in a variety of applications.

Micromachining technologies have become widely available in the past decade. Silicon micromachining in particular enables full integration of mechanical and sensing elements, offering cost effective production of small transducers with the potential of producing an array of sensors as a single integral unit.

Publication US 2002/0028456 A1 discloses a sensor array disposed on a substrate to measure various material properties of samples deposited on the substrate. Samples may be deposited on the sensor in solution or by vapor deposition. Properties, which can be measured, include temperature, heat capacity, thermal conductivity, thermal stability, dielectric constant, viscosity, density, elasticity, capacitance and magnetic properties.

WO 00/20850 teaches a multi-sensor device for gravimetric chemical measurements of gaseous or vapor-state analytes comprising a substrate and a plurality of sensors made from piezoelectric elements realized with thick-film technology on the substrate. The sensors are coated with sensitive coatings for absorbing the analytes.

U.S. Pat. No. 5,983,711 discloses a temperature-controlled gravimetric moisture analyzer comprising a sample holder attached to a weighing mechanism, a temperature sensor and a heater and controller responding to the output signal of the temperature sensor. This patent does not disclose an array of weighing devices, however.

WO 03/071241 discloses a spring scale for micro-weighing comprising a load platform suspended by at least three flexural springs in a surrounding frame, with bridge-connected strain gauges for measuring strain on one side of the flexural springs. There is no suggestion of an array of weighing devices, however.

U.S. Pat. No. 4,566,326 teaches an automatic adsorption and desorption analyzer for performing measurements on a plurality of powder samples using a plurality of sample cells with associated valves, controls and sensors. The analyzer can measure surface area, total pore volume, micropore volume, average pore radius, and pore-size and surface-area distributions substantially simultaneously on a plurality of samples. This analyzer represents known art in accomplishing the purposes of the present invention.

The art does not suggest, however, either an apparatus or a method for effecting mass analyses on an array of samples contained in distinct sample holders.

SUMMARY OF THE INVENTION

The present invention provides an apparatus and a method for mass analysis of each of an array of samples contained in an array of distinct sample holders positioned to interact with a plurality of sensors providing output signals comprising mass data on the array of samples. Through such analyses, the invention enables the rapid determination of a variety of properties of the samples related to their mass. Subsequent analyses of further arrays of samples also are expedited.

In a more specific embodiment, the invention provides an apparatus for mass analyses of each of an array of samples comprising an array of distinct sample holders containing the samples positioned to interact with a plurality of microbalances providing output signals comprising mass data on the array of samples.

In a yet more specific embodiment, the invention provides an apparatus for mass analyses of each of an array of samples comprising an array of distinct sample holders containing the samples positioned to interact with a plurality of spring scales providing output signals comprising mass data on the array of samples.

In another specific embodiment, the invention provides an apparatus for mass analyses of each of an array of samples comprising an array of baskets containing the samples positioned to interact with a plurality of microbalances providing output signals comprising mass data on the array of samples.

In an alternative embodiment, the invention provides a method for mass analysis of an array of samples by placing the array in an array of distinct sample holders, positioning the sample holders to interact with a plurality of sensors providing output signals comprising mass data on the array of samples, and determining the mass of each of the samples from the output signals.

In a more specific alternative embodiment, the invention provides a method for mass analysis of a multitude of samples by placing the samples in an array of distinct sample holders, positioning the sample holders to interact with a plurality of sensors providing first output signals comprising mass data on the array of samples, subsequently exposing the array of samples to a change in environmental conditions, subsequently measuring second output signals from the array of samples, and determining one or more properties of each of the samples by comparing the output signals from the array of samples before and after the change in environmental conditions.

BRIEF DESCRIPTION OF THE DRAWINGS

FIG. 1 illustrates a broad embodiment of the apparatus of the invention comprising a small array of six sample holders interacting with a plurality of the same number of sensors.

FIG. II illustrates the apparatus of the invention in an embodiment comprising a spring scale in an element of an array.

FIG. III shows an example of a bridge circuit that can be used in mass analysis.

FIG. IV is a cross-sectional side-view illustration of a spring scale connected to a base part.

FIG. V illustrates the apparatus of the invention in an embodiment comprising a suspended basket in an element of an array.

FIGS. VI-A and VI-B and VII-A and VII-B illustrate a alternative arrangements of the microbalance as a cantilever.

DETAILED DESCRIPTION OF THE INVENTION

In summary, the present invention provides an apparatus and a method for mass analysis of each of an array of samples contained in an array of distinct sample holders positioned to interact with a plurality of sensors providing output signals comprising mass data on the array of samples. Although elements of the method and associated apparatus are described in the singular, it is to be understood that two or more parallel or series sets of each element or of the entire apparatus are within the scope of the invention.

The "array" of samples and sample holders encompasses at least four (4), more usually six (6) or more, generally at least eight (8), and optionally forty-eight (48) or more samples and holders. It is within the scope of the invention that some multiple of these numbers is contained in the array such as 24, 96, 392, or 1264 arranged in a row-and-column formation similar to that of a microtiter tray. Preferably the sample holders are spatially separated such that individual members of the array are addressable separately. The "plurality" of sensors is within the same numerical ranges as described for the "array," and preferably the number of sensors is the same as the number of samples and sample holders. Considering the invention in relation to the known art using parallel or sequential analysis, the equipment and/or time required for analyses according to the known art would be relatively expensive.

By "sample" is meant a substrate for which mass analysis is desired. These substrates are often solids, but not necessarily limited to solid materials, for example liquids, gels, slurries, and the like. Possible examples of liquid applications are with respect to ionic liquids, monitoring gas solubility in liquids, etc. Possible examples of solid samples comprise, without limiting the invention, ceramics, molecular sieves, other inorganic compounds, composites, metals and metal alloys, intermetallics, carbon, ionic solids, molecular solids, covalent network solids, organometallic materials, organic polymers and combinations thereof. Substances for which surface properties are important are preferred, and especially preferred substances comprise metal oxides, molecular sieves and catalytic agents.

Sample form is not critical to the definition of the invention. If a solid materials, the sample may be a single solid monolith, or as particles, films, plates, discs, beads, spheres, rods, wires, or any form suitable for the analysis to be conducted. Preferably the solid sample is in the form of particulates, and a fine-powder form of sample is especially preferred. In a fine powder, the average particle size typically will range from about 0.01 µm to about 1000 µm, and more usually will be between about 0.1 µm to about 100 µm.

The present invention comprises an array of sample holders, with a sample holder or container provided for each sample to be analyzed. The sample holder may be any device which can contain a sample and which is transferable to and from a sensor to be defined hereinafter. Preferably the sample holder or container provides a concave surface facing upward which contains the sample without risk of substantial spillage. Suitable configurations comprise, without limitation, pans, cups, saucers, plates, indentations and depressions. Alternatively, the sample holder may comprise a basket which is supported on a sensor by a hook, loop, ring, clip, clasp or other fastener. Advantages of placing the sample in a sample holder to be transferred to and from a sensor include:
- avoidance of sensor contamination by direct contact with the sample, and
- the ability to effect measurements in parallel with the handling of samples, and cleaning of sample holders through multiple sets of sample holders.

Any material that does not adversely affect results of the analysis is suitable for the sample holder. Preferably the surface of the sample holder that contacts the sample is stable and inert to the sample at all conditions of the method of the analysis. One or both of ceramic and metal materials are especially preferred for the sample holders.

Optionally, input to the analysis is provided through the sample holder. For example, without limitation, the sample holder may comprise a thermally conductive material through which heat may be provided to the sample or the temperature of the sample measured. Alternatively, electrical energy may be transmitted to the sample through the sample holder. It is within the scope of the invention that the sample holder is coated or layered with material that aids in the analysis through physical or chemical action. Further, the sample itself could be coated onto the surface of the sample holder through chemical or physical bonding, evaporation and the like.

Following the analyses of the array of samples, each analyzed sample may be unloaded from the respective sample holder and a fresh array of samples then is placed on the array of sample holders. Preferably one or more additional arrays of samples on additional sample holders have been prepared while the analyses are being effected such that the additional array of samples may be positioned to interact with the plurality of sensors while the analyzed samples are being unloaded from their respective sample holders. Optimally, the array of sample holders is contained in a tray which may be lowered toward the apparatus comprising sensors to place the sample holders in position on the sensors. In this manner, the preparation and unloading of samples will not delay the analysis of samples, and the apparatus comprising sensors is utilized more effectively.

FIG. I illustrates an array of six distinct sample holders 1 positioned to interact with a plurality of six sensors 2 providing output signals comprising mass data on the array of samples. The sensors comprise spring scales contained in a frame 3 as described hereinbelow for one individual unit of the six sample holders and spring scales. As discussed hereinabove, the "array" or "plurality" comprises at least 4 such units, and preferably a larger number of units.

Suitable sensors include any type that can measure mass changes and support a sample holder. Sensor materials comprise one or more of metals, silicon, other semiconductor materials, glasses, carbon, polymers, membranes and the like, with semiconductor materials such as silicon being particularly favored. Preferred sensors of the invention comprise microbalances, in particular spring scales as described in International Publication WO 03/071241 which is incorporated herein in its entirety by reference thereto. The preferred spring scale comprises a load platform suspended in a surrounding frame by means of at least three flexural springs, with bridge-connected strain gauges arranged for measuring strain on one side of the flexural springs.

FIG. II shows a preferred embodiment of the invention schematically in a view from above. A spring scale, in this example having the shape of a square, has in its center a load platform 1 upon which the sample holder as shown in FIG. I is placed. The load platform 1 is suspended in a frame 2 by means of flexural beams or flexural springs 3, which beams/springs are in the shown example arranged along each side edge of the load platform, and slits 5 and 6 have been etched or machined to provide the flexural beams 3 in such a manner that a slit has one slit part 5 on the outside of the flexural beam 3 and a continuing part 6 on the inside of the next flexural beam 3. In such a construction the flexural beams 3 become relatively long and compliant, i.e. the load platform 1 can be given a deep swing. Each flexural beam 3 is situated in a gap between the frame 2 and the load platform 1, which gap is defined by the slit parts 5 and 6. Each flexural beam 3 has an attachment spot 7 to the load platform 1 situated directly opposite the attachment spot 8 of an adjacent flexural beam to frame 2. Reference 4 designates sensors for recording a load on the load platform 1. When a sample holder is placed on the load platform 1, the platform will sink in a direction away from the observer, and the flexural beams 3 will bend and assume a shape similar to a shallow S. The load platform will then at the same time rotate somewhat about an axis perpendicularly to the plane of the load platform, as the length of the beams 3 remain substantially constant.

With the above-mentioned S-shape in the flexural beams 3 when the platform is loaded, the most intense mechanical stresses in the beams are found in the crossing areas to frame 2 and load platform 1 (i.e. at the attachment spots 7 and 8). It is therefore favorable to mount strain gauges 4 for example as shown in FIG. II. Alternatively, the strain gauges can be mounted in the crossings to the load platform instead of crossings to the frame, but this will require longer leads from the strain gauges and to the signal processing equipment. In the way the strain gauges 4 have been mounted in FIG. II, all four gauges are positioned in the same direction in order to optimize connecting the sensors in a Wheatstone bridge. The sensors/gauges can alternatively be mounted in different directions; for example turning two of them 90° relative to the other two with modification of the bridge connection.

The strain gauges 4 can be arranged as separate sensors on top of the crossings in question (attachment spots 8 or 7), by means of depositing and pattern forming, or by gluing ready resistors. Alternatively, strain gauges in the form of piezo-resistors can be manufactured as an integral part of a favored silicon structure or arranged as a surface element in any suitable manner.

In a favorable embodiment of the invention the load platform, flexural springs and frame are shaped as one micromachined or etched piece of semiconductor material; optimally this material is silicon. The strain gauges, preferably piezo-resistive resistors arranged on a crossing between the flexural spring and the frame or load platform, may be integral in the piece of the solid material. The semiconductor material, primarily for shaping the spring scale, thus also may be applied to shaping the sensor elements used for detecting a load.

FIG. III shows an example of a bridge circuit that can be used for providing a mass analysis by means of the scale of the present invention. The bridge circuit shown is a Wheatstone bridge adapted to the case of FIG. II, in which every strain gauge 4 is mounted in the same direction. The strain gauges are in the form of resistors 4, and the Wheatstone bridge circuit is completed by a current source (battery) 11 and a measurement instrument 12. This is a standard type circuit, but other bridge circuit variants may be used in connection with other embodiments with other strain gauge configurations.

In a broad embodiment, the spring scale according to the invention is not restricted to a single piece or from semiconductor material. Further, many geometrical shapes may be used as long as the central load platform is suspended by at least three flexural springs that connect the load platform with a surrounding frame.

One alternative embodiment is a substantially circular load platform inside a circular opening in a frame. Curved flexural beams or springs are attached to the load platform and frame respectively. Usually the attachment spots are situated directly opposite each other, but they may overlap or even spiraling past/along each other in the gap between the load platform and the frame. Strain gauges as before are situated at the flexural beam attachment spots to the frame or platform, i.e. at the spots where surface stress is at the most intense in a weighing operation.

Another possible configuration comprises a triangular load platform and three flexural beams between the load platform and the frame. Strain gauges, mounted for instance in the three attachment spots can be connected in a modified bridge connection. Thus, a plurality of geometrical shapes will satisfy the requirements of the invention.

A construction with four flexural springs is preferable, for at least three reasons:
1. In a Wheatstone bridge of standard type, just four resistors are included.
2. To have a stable load platform, one should not use too many beams.
3. For a micro-scale manufactured in silicon, it is a point that silicon (100) wafers have four-fold symmetry and this entails that the piezo-resistors should be positioned along the [011] or [011] directions.

FIG. IV shows schematically a cross-section through a central part of a spring scale comprising a platform 1 upon which a sample holder has been placed in accordance with the FIG. I embodiment of the present invention. The central area comprising the platform is thinned down relative to the frame area 2 which may be substantially thicker. The flexural beams 3 appear such that two beams can be seen in a side view and exhibit an S-shape.

The embodiment shown in FIG. IV also shows an optional base part 4 which can be made of glass and attached to the frame 2 by means of anodic bonding. By making the base part 4 extend in under the load platform 1, it forms a swing-down limit for load platform 1 as a safety function for the flexural springs 3. As shown, the base part 4 is also may be equipped with a central opening 5 for regard to inspection and cleaning. Above the scale, an optional roof 6 may be provided as an end stop as protection and for possible swings upward for load platform 1. Optimally, there is a central opening 7 in the roof in order that an object to be weighed can be laid down on the load platform. The roof may be glass and fixed to the silicon structure 8. Reference 9 designates a contact section for signal leads from the strain gauges. The roof may be glass and fixed to the base part 4.

In an alternative embodiment, the sample holder is placed on a microbalance as a hanging basket. An example of this embodiment is illustrated in FIG. V. A support 1 comprises an array of microbalances, one microbalance 2 being shown in the Figure. A sample holder 3 is suspended as a hanging basket from the microbalance via a loop 4 attached to the microbalance and a wire 5 from the loop to the basket. In this embodiment, the hanging basket and sample holder, attachment to the microbalance, and means for connecting the attachment and hanging basket may be any of those known in the art which can contain the sample and remain stable under the conditions of the mass analysis.

Although it is preferred that the mass analysis be conducted using strain gauges, and particularly piezoresistors in a Wheatstone bridge as described hereinabove, it is within the scope of the invention that other methods of detecting the deflection of the microbalance may be used. These methods include but are not limited to the use of optical or magnetic detectors. In one embodiment, deflection signals from each of the microbalances are determined using a photodetector.

In yet another alternative embodiment, the microbalance comprises a cantilever; two examples are identified in FIGS. VI and VII. In FIGS. VI-A and VI-B, a cantilever 1 comprises a ring configuration 2 for suspending a sample holder 3 which preferably is a hanging basket. The basket is attached to the ring 2 of the cantilever by any suitable means, preferably via a wire 4. The bridge 5 of the cantilever comprises strain gauges 6 and 7 in the form of piezoresistors to effect the mass analysis of a sample placed in the sample holder 3.

In FIGS. VII-A and VII-B, a cantilever 11 comprises a sling configuration 12 for suspending a sample holder 13 which preferably is a hanging basket. The basket is attached to the sling 12 of the cantilever by any suitable means, preferably via a wire 14. The bridge 15 of the cantilever comprises strain gauges 16 and 17 in the form of piezoresistors to effect the mass analysis of a sample placed in the sample holder 13.

Signals from the microbalances are read through a readout board and processed by a microcomputer. A temperature signal can be used to compensate for temperature dependence of the sensor. The temperature signal can be provided from a separate resistor or diode, or one can monitor the total bridge resistance.

In measurements where the sample is heated or cooled, thermoelectric voltages at junctions can affect the measurements. This can be compensated by periodically switching off the power source (11) and subtracting the output from the measurements. One can also use a compound AC excitation and a lock-in measurement.

The computer is equipped with suitable software for designing the test, controlling the environment, and acquiring and analyzing data to determine the properties of the samples.

Preferably the mass analysis is effected in a controlled environment. The environment can be controlled when the samples and sample holders are placed within one or more suitable sealable chambers which isolate the sample holders from uncontrolled environmental conditions. Environmental conditions to be controlled comprise, without limitation, pressure, temperature and fluid composition, for example but not limited to gases surrounding the samples and sample holders. Suitable pressures comprise between about $10^{-10}$ Torr to 300 bar, and preferably from about $10^{-6}$ Torr to 150 bar; temperatures generally are in the range of about $-200°$ to about $1000°$ C., and more usually less than about $500°$ C. Any suitable heating or cooling device known in the art may be used to control the temperature.

The composition of the fluid medium in the controlled environment may be varied for weighing the samples and to effect tests described hereinafter. In the case of the fluid medium, suitable gases include without limitation one or more of nitrogen; carbon monoxide; carbon dioxide; ammonia; $SF_6$; argon, helium or other inert gases; and butane, pentane or other hydrocarbons.

Often environmental conditions are varied over time in order to determine sample properties as described hereinbelow. The variation may comprise one or more of a substantial change in temperature, a change in pressure, and a change in compositional environment. For example, one or more properties may be determined by the steps of measuring first output signals from the array of samples, subsequently exposing the array of samples to a change in environmental conditions, subsequently measuring second output signals from the array of samples, and determining one or more properties of each of the samples by comparing the first and second output signals. The steps may be repeated on the tested samples through sequences of subsequently exposing the array of tested samples to a further change in environmental conditions, subsequently measuring further output signals from the array of samples, and determining one or more properties of each of the samples by comparing the output signals from the further testing. The deflection signals of the array of microbalances can be compared before and after the change in environmental conditions. Preferably this is effected using a known sensor curve for each of the plurality of spring scales.

Mass also can be measured by recording the eigenfrequency of the loaded balance and relating this according to the equation $\omega=\sqrt{k/m}$ where k is the spring stiffness, and m is the effective mass. The vibrations can be induced by external agitation of the whole array followed by monitoring the free oscillations of each balance. The method can be used for calibration, or measurements when large offsets are superimposed on the transducer output (e.g. by thermoelectric effects).

Uses:

The microbalance of the invention could have one or more of a variety of uses in addition to sample weighing. For example, monitoring weight changes in samples due to changes in environment or as function of time can yield data on surface area, pore size and volume, acidity/basicity and metal function among other characteristics. Changes in the environment due to mass changes in the samples can be monitored, and the microbalance can be used for reactivity testing.

The microbalance array by itself could be used to weigh samples for a sample array. This function could be used as a preparation step for another operation, for example characterization analysis, reactivity test, or synthesis. Also the weight change alone could be a key part of an analysis involving exposure of a set of samples to a specific set of conditions (e.g. coke deposition for a reactivity test, hydrogen uptake at high pressure). Other possible uses include, without limitation:

Isotherms from Physisorbed Probe Molecules:
  Surface Area
    Either the Langmuir equation (single layer adsorption) or the BET (Brunauer, Emmett, and Teller) equation (multi-layer adsorption) or any other appropriate method of determining or calculating is used to derive a surface area from isotherm data. Typically nitrogen is used as the adsorbate.
  Pore Volume
    Using the Kelvin Equation, the amount of adsorbate is expressed as a corresponding volume of pores.
  Pore Size Distribution
    Typically the desorption isotherm along with the Kelvin Equation is combined with various ways to estimate an adsorbate film thickness as a function of its partial pressure. These equations are used to estimate the distribution of pore sizes for a sample.
  Adsorption Capacity
    For a given set of conditions (vapor pressure and temperature), the amount of probe molecule adsorbed is measured. This value is of interest for evaluating or comparing materials. Typical examples are selective adsorption and gas-storage applications. Also of interest is the adsorption capacity for a single adsorbent using a set of probe molecules of various kinetic diameters. This is analogous to McBain measurements, and helps to classify the pore size of a material.

Adsorption Kinetics (diffusion)

By measuring the uptake rate of a probe gas, an estimate of the diffusion constant for the adsorbent/adsorbate system can be made. When made at a range of temperatures, this method can be used to determine an activation energy for diffusion.

Heats of Adsorption

Measurement the adsorption capacity at several temperatures allows for calculating the heat of adsorption for a given sample and adsorbate.

Isotherms from Chemisorbed Probe Molecules

Acidity

The amount of a probe base adsorbed by a sample can be used to estimate the number of acid sites for the sample. By making either adsorption measurements at several temperatures, or by measuring the amount of base desorbed as a function of temperature, the acid strength distribution for a sample can be estimated.

Example Probe Molecules: $NH_3$, CO, Pyridine, Trimethylphosphine

Number of Acid Sites

Strength of Acid Sites

Basicity

Similar to acidity, but using probe molecules to characterize basicity.

Example Probe Molecules: Ethene, Propene, 1-Butene

Number of Basic Sites

Strength of Basic Sites

Metal Function

By selecting the appropriate probe molecule, the metal or metals loaded on a sample can be characterized. If the amount of metal loaded on the sample is unknown, the amount of a probe molecule adsorbed by materials containing a metal function can be used to determine the amount of exposed metal atoms. If the metal loading is known, this same information can be used to determine what percentage of the metal is accessible for catalytic reactions. This type of information would be very useful to characterize the metal dispersion as a function of impregnation conditions, secondary treatments (e.g. hydrothermal), and deactivation due to carbon deposition.

Mass changes in samples due to redox of metals on a sample can also be used to characterize metal content, dispersion, and activity.

CO Uptake $H_2S$ Uptake $H_2/O_2$ Redox/Uptake

Atmospheric Sampling

A set of materials could be placed in the microbalance array, and exposed to a process stream or gas from the surrounding environment in order to characterize the process stream or gas. One example would be to select a set of microporous materials covering a range of pore sizes. Each unique material would only adsorb molecules in a specific size range. By simultaneously comparing the amount adsorbed for each material, the gas stream can be characterized.

Likewise, materials containing specific cations that are known to change adsorption properties could also be used to characterize a gas stream.

Reaction Pulse Experiments

Coking

A reactant stream can be pulsed over a set of samples, and the amount of carbon deposited for a given pulse can be measured. This provides information about the reactivity, and deactivation rate for a set of samples.

Redox

Exposing a set of samples to an oxidizing and/or a reducing environment while measuring weight changes gives information about redox activity and capacity. This would be similar to the metals test mention above.

Polymerization

Information about activity and kinetics of polymerization catalysts or initiators can be estimated by exposing such materials to an oligomerizable or polymerizable gas.

Combined Techniques

The combination of two or more techniques for in situ analysis of properties of an array of samples would be a particularly valuable feature of the present invention.

IR Thermography+Microbalance Measurement

The microbalance measurement could be combined with IR thermography measurements. In this experiment a base (or acid) is introduced to the sample array. During the exposure, the microbalance would be monitoring the weight changes, and the IR camera would be monitoring the heat changes and heat of adsorption. The use of both techniques simultaneously provides much more information than each technique being run independently. The information from both measurements can be combined to determine the number and strength of acid (or base) sites in a material.

Acidity

Basicity

Reactivity

Temperature+Microbalance Measurement

By monitoring the weight changes as a function of temperature, the system could function as a combi-tga (thermo-gravimetric analysis). One could monitor phenomena such as water desorption as a function of temperature, template oxidation for zeolites (passing air during the temperature ramp), carbon burn kinetics for regeneration studies.

XRD+Microbalance Measurement

The microbalance measurement could be combined with a combi-xrd (x-ray diffraction) measurement. A set of samples could be exposed to a probe gas in this system which would allow structural information to be measured as a function of the amount of probe gas adsorbed. Some example uses could be:

Impact of water on unit cell size

Impact of a given hydrocarbon on unit cell size

Impact of carbon (coke) on unit cell size (in-situ coke burring)

The above description and examples are intended to be illustrative of the invention without limiting its scope. The skilled routineer will readily understand how to extrapolate parameters of the disclosure to other embodiments of the invention. The invention is limited only by the claims set forth herein.

The invention claimed is:

1. An apparatus for mass analysis of each of an array of samples comprising an array of distinct sample holder baskets containing the samples and a plurality of sensors, wherein each sample holder basket is suspended from a corresponding sensor, the plurality of sensors providing output signals comprising mass data on the array of samples contained in the sample holder baskets.

2. The apparatus of claim 1 wherein the plurality of sensors comprises an array of microbalances.

3. The apparatus of claim 2 wherein the array of microbalances comprises an array of spring scales.

4. The apparatus of claim 3 further comprising a frame prepared by micro-machining a single sheet of material wherein the array of spring scales is integral with the frame.

5. The apparatus of claim 3 wherein each of the spring scales comprises a load platform suspended by one or more flexural springs each having a bridge-connected strain gauge arranged for measuring strain on one side of each of the one or more flexural springs.

6. The apparatus of claim 5 wherein each of said strain gauges is a piezo-resistive resistor.

7. The apparatus of claim 1 wherein the array of sample holder baskets are transferable to and from the sensors.

8. The apparatus of claim 2 further comprising a compound alternating-current signal generator and filter with a lock-in amplifier for detection of a deflection signal at an encoding frequency.

9. The apparatus of claim 1 wherein the basket is suspended from the sensor by a fastener.

10. The apparatus of claim 9 wherein the fastener is selected from the group consisting of a wire, hook, loop, ring, clasp, and clip.

11. The apparatus of claim 2 wherein the array microbalances comprise an array of cantilevers.

12. The apparatus of claim 11 wherein the cantilevers comprises strain gauges.

13. The apparatus of claim 12 wherein the strain gauges are piezoresistors.

* * * * *